US00PP29147P2

(12) United States Plant Patent
Dodd et al.

(10) Patent No.: US PP29,147 P2
(45) Date of Patent: Mar. 27, 2018

(54) APPLE TREE NAMED 'MAIA8'

(50) Latin Name: *Malus×domestica*
Varietal Denomination: MAIA8

(71) Applicants: William Dodd, Newcomerstown, OH (US); David Doud, Wabash, IN (US); John Mitchell Lynd, Pataskala, OH (US); Gregory Miller, Carrollton, OH (US)

(72) Inventors: William Dodd, Newcomerstown, OH (US); David Doud, Wabash, IN (US); John Mitchell Lynd, Pataskala, OH (US); Gregory Miller, Carrollton, OH (US)

( * ) Notice: Subject to any disclaimer, the term of this patent is extended or adjusted under 35 U.S.C. 154(b) by 0 days.

(21) Appl. No.: 15/330,371

(22) Filed: Sep. 12, 2016

(51) Int. Cl.
*A01H 5/08* (2006.01)

(52) U.S. Cl.
USPC ..... Plt./161

(58) Field of Classification Search
USPC ..... Plt./161
CPC ..... A01H 5/0875
See application file for complete search history.

*Primary Examiner* — Kent L Bell

(57) ABSTRACT

A new and distinct variety of apple tree was identified from a population of seedlings derived from a cross of 'Goldrush' and 'Sweet 16'. The new variety, named 'MAIA8', is distinct from 'Goldrush' as 'MAIA8' ripens late-September, 5 weeks before 'Goldrush'. Unlike 'Goldrush', 'MAIA8' has scarlet red skin (R.H.S. Colour Chart Red-Purple Group 60B). While 'Goldrush' will keep for more than 20 weeks in normal 35° F. storage, 'MAIA8' will only keep for approximately 10 weeks in normal 35° F. storage. 'MAIA8' is distinct from 'Sweet 16' as 'MAIA8' is much more precocious, setting fruit in the first year of planting. 'Sweet 16' typically does not set fruit until 2 years after planting. The fruit of 'MAIA8' adheres to the tree for approximately 6-7 weeks past fruit maturity, while 'Sweet 16' fruit will abscise from the tree within 2 weeks of maturity. 'MAIA8' fruit are medium sized, crisp, with unique and complex sweet-tart flavor with peach, pear, and strawberry flavor tones.

3 Drawing Sheets

Latin name of the genus and species of the plant claimed: *Malus×domestica.*

Variety denomination: 'MAIA8'.

BACKGROUND OF THE INVENTION

A new and distinct variety of apple tree was identified from a population of seedlings derived from a cross of 'Goldrush' (U.S. Plant Pat. No. 9,392) and 'Sweet 16' (not patented—originating from a cross of 'Northern Spy' (not patented) and 'Malinda' (not patented) made in Minnesota, US, and released as a variety in 1973). This cross was made as a part of the Midwest Apple Improvement Association apple breeding project. This superior seedling tree was identified in a population of seedlings from this cross at Belleville, Ill.

The seedling tree was planted as a 1-year-old tree at Belleville, Ill., in 2001 and grown among a population of several hundred siblings. Evaluations of fruit quality and tree growth parameters were begun in 2005 and this seedling was identified over several years as superior based upon tree growth habit, precocity, superior fruit quality and harvest time. Utilizing grafting reproduction, the new apple tree variety was asexually propagated by John Mitchell Lynd at Pataskala, Ohio and has been observed to remain true to the description set forth herein.

The new variety, named 'MAIA8' is distinct from parent 'Goldrush' as 'MAIA8' ripens late-September, 5 weeks before 'Goldrush' (FIG. 1). Unlike 'Goldrush' 'MAIA8' has scarlet red skin (R.H.S. Colour Chart Red-Purple Group 60B). While 'Goldrush' will keep for more than 20 weeks in normal 35° F. storage, 'MAIA8' will only keep for approximately 10 weeks in normal 35° F. storage (FIG. 1). The closest comparison variety to 'MAIA8' is 'Sweet 16'. 'MAIA8' has far better crimson red skin color, better keeping quality (4-6 weeks longer than 'Sweet 16'), with a similar harvest date. 'MAIA8' is further distinct from 'Sweet 16' as 'MAIA8' is much more precocious, setting fruit in the first year of planting. 'Sweet 16' typically does not set fruit until 2 years after planting. The fruit of 'MAIA8' adheres to the tree for approximately 6-7 weeks past fruit maturity, while 'Sweet 16' fruit will abscise from the tree within 2 weeks of maturity. 'MAIA8' fruit (FIG. 2) are medium sized, crisp, with unique and complex sweet-tart flavor with peach, pear, and strawberry flavor tones.

BRIEF DESCRIPTION OF THE DRAWINGS

The accompanying photographs show typical specimens of the new variety depicted in color as true as is reasonably possible.

FIG. 1. Shows that 'MAIA8' is distinct from parents in both harvest time and storage window.

DETAILED BOTANICAL DESCRIPTION

Figure 1:
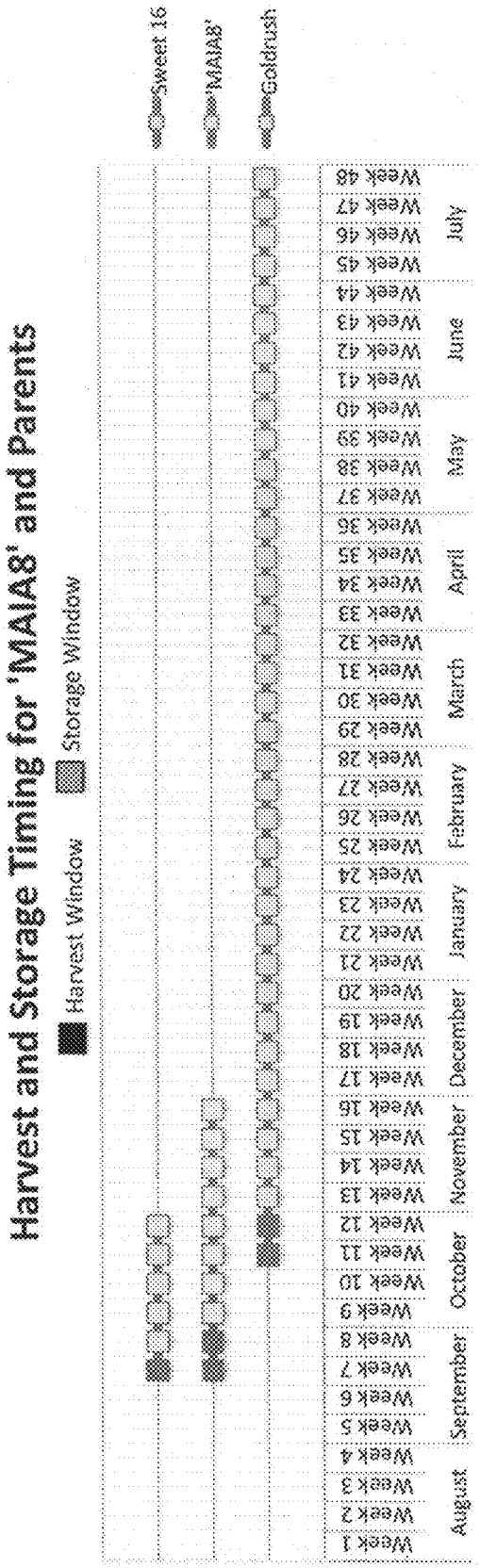
FIG. 1 was created from harvest and storage data from Pataskala, Ohio, and Carrollton, Ohio.
Figure 2:
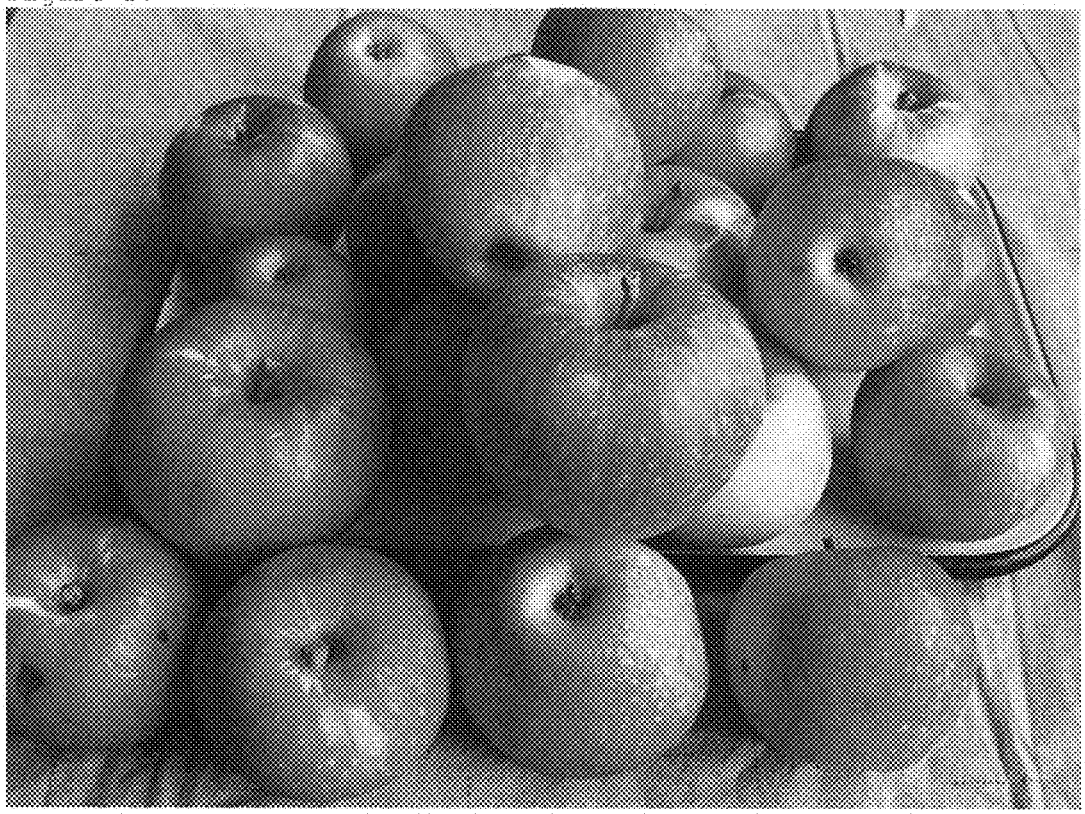
FIG. 2. Typical fruit of 'MAIA8' post-harvest.
Figure 3:
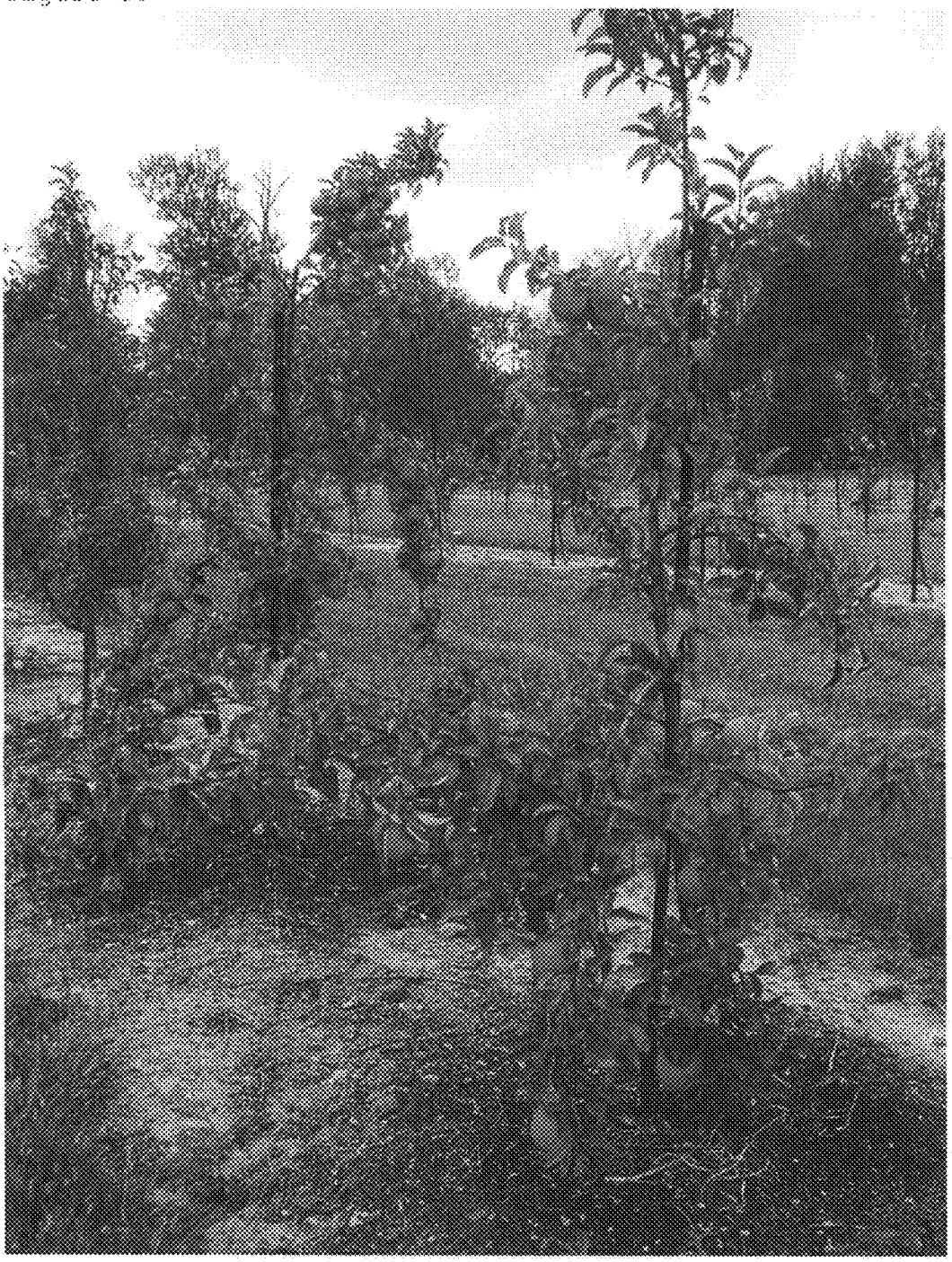
FIG. 3. Typical 'MAIA8' trees bearing fruit in September in Ohio.

Color references are made to The Royal Horticultural Society Colour Chart (R.H.S.) 2001 Edition.

Parentage: 'Goldrush' female parent and 'Sweet 16' male parent; controlled cross made by Greg Miller at Pataskala, Ohio in 1999.

Original seedling tree:

*Age.*—17 years.

*Size.*—Medium, 15' height, 15' spread.

*Vigor.*—Moderate to weak.

*Form.*—Round, spreading.

*Production.*—Very productive.

*Growth type.*—Spindle tree growth form, productive spurs located throughout tree.

*Bearing.*—Annual.

Trunk:

*Original seedling tree size.*—7 cm at 15 cm height.

*Bark color.*—Grey-Brown 199C.

*Lenticel.*—Oblong, 4 mm×1.5 mm.

*Lenticel color.*—Greyed-Yellow 161A.

*Lenticel density.*—4 lenticels/$cm^2$.

Branches:

3 *year old.*—8 mm in diameter, branch angle 70-80°, Grey-Brown N199C; typical branch length of 25-35 cm.

2 *year old.*—5 mm in diameter, branch angle 70-80°, Grey-Brown N199B; typical branch length of 20-35 cm.

1 *year old.*—3-4 mm in diameter, branch angle 70-80°, Brown Group 200B; typical branch length of 15-23 cm.

Leaves:

*Size.*—Length 70 mm; width 30 mm.

*Texture.*—Leathery, crisp.

*Form.*—Ovate.

*Base.*—Cuneate.

*Apex.*—Acute.

*Adaxial surface pubescence.*—None.

*Abaxial pubescence.*—Pubescent.

*Adaxial surface color.*—Yellow-Green 146D.

*Abaxial surface color.*—Yellow-Green 145D.

*Veination.*—Pinnate, 8-9 major veins, mainly alternate.

*Margin.*—Serrate, rounded at tips.

*Petiole length.*—2.5 mm.

*Petiole width.*—3 mm.

*Petiole abaxial color.*—Greyed-Purple 184B to Greyed-Green 193A.

*Petiole adaxial surface color.*—Greyed-Purple 184B to Greyed-Green 193A.

*Petiole groove.*—Very shallow, depth 0.1 mm.

*Stipules.*—Uncommon, highly variable.

*Leaf glands.*—None observed.

Leaf buds:

*Length.*—3 mm.

*Width.*—2 mm.

*Shape.*—Both lateral and terminal buds pointed with imbricate scales.

*Color.*—Yellow-Green 145A with Brown Group 200A overtones.

*Placement on branch.*—Alternate.

*Internode distance.*—20 mm.

Spurs: Present on 2 year and older wood.

*Length.*—Varies from 12-90 mm.

*Width.*—4-5 mm.

Flowers at popcorn stage:

*Pedicel.*—Length 10-20 mm; diameter 1-2 mm.

*Pedicel color.*—Greyed-Green 191A.

*Bud.*—Length 9-12 mm; width 8-11 mm.

*Bud color.*—Red-Purple Group 63B to Red-Purple Group 69C.

Flowers at full bloom:

*Bloom time.*—Depends on spring temperatures, but with 'Golden Delicious' typically during $4^{th}$ week of April in northern Ohio.

*Bloom period.*—Depends on spring temperatures but first spur blossoms and then lateral blossoms on one-year wood; approximately 7 days.

*Presentation.*—Showy.

*Fragrance.*—Aromatic.

*Fertility.*—Fertile.

*Number of flowers per cluster.*—4-6 with 5 typical.

Petals:

*Arrangement.*—bases overlapping; 5 petals/flower; each petal 13-19 mm length; 10-16 mm width.

*Color.*—Upper surface (inside) Grey Group NN155B; lower surface (outside) Grey Group NN155B with Greyed-Purple 186B pronounced as flower begins to open and then fading as flower completely opens.

*Shape.*—Broadly ovate, abruptly cuneate at junction with receptacle.

*Petal apex.*—Predominantly rounded with some fluting.

*Veins.*—Distinct, minor lateral veins at base.

*Margins.*—Smooth edge and continuous.

*Texture.*—Soft.

*Receptacle.*—Length 6-7 mm; width 4-5 mm; color Greyed-Green 191A with Red-Purple 63B.

*Pedicel.*—Length 14-20 mm; width 2 mm; color Greyed-Green 191A.

*Sepals.*—5/flower; wedge-shaped; sharply pointed; length 5-7 mm; width 2-3 mm at widest point; adaxial and abaxial color Greyed-Green 196B with Greyed-Green 187C at tips.

*Stamens.*—15-20 in number.

*Anthers.*—length 1.5-2 mm; width 1.5 mm; color Yellow Group 4C.

*Pollen.*—Present and abundant; color Yellow Group 10C.

*Filaments.*—Length 5-9 mm, increasing in length as flower matures; width 0.5 mm; color Greyed-Green 155C.

*Pistil.*—Held lower than anthers in majority of blossoms; color Greyed-Green 157A.

*Ovary.*—Length 4 mm; width 4 mm; color Green 143B.

*Style.*—Length 9-10 mm; the 5 styles are fused in bottom 2 mm only; width 1 mm; color Greyed-Green 199C.

*Stigma.*—Width 0.5 mm; color Greyed-Green 193A.

Pollination requirements: Requires cross-pollination from diploid varieties with overlapping bloom; will pollinate diploid varieties of overlapping bloom.

Fruit:

*Maturity when described.*—6 week storage.

*Date of picking.*—Oct. 7, 2015.

*Size.*—Axial diameter 68-83 mm; transverse diameter 26-71 mm.

*Fruit weight.*—122-234 g, average 165 g.

*Form.*—Oblate conic.

*Cavity.*—Acuminate, deep, russet deep inside cavity does not extend out.

*Basin*.—Narrow width, medium depth, symmetrical; width 22 mm.
*Calyx*.—Open, sepals small-recurved.

Skin:
*Thickness*.—Medium-thick.
*Tendency to crack*.—None.
*Lenticels*.—Round shape; 1-1.2 mm diameter.
*Color*.—Red-Purple 60B.
*Stripes*.—Light striping, dimensional spotting.
*Ground color*.—Yellow Group 8B.

Flesh:
*Aroma*.—Sweet, spicy.
*Color*.—White Group 155A.
*Texture*.—Firm, chewy.
*Eating quality*.—Excellent.

Core:
*Locule number per fruit*.—5.
*Bundle area*.—Average 1155 $mm^2$.
*Bundle*.—Conspicuous.
*Carpel axial length*.—Average 11 mm.
*Seed cells*.—Hard, tough.

Seeds:
*Number perfect*.—10-11.
*Number in one cell*.—2.
*Length*.—8 mm.
*Width*.—5 mm.
*Color*.—Greyed-Orange 166A.

Stem:
*Length*.—20-28 mm.
*Width*.—2-4 mm.
*Color*.—Greyed-Orange 163C.

Use: Fresh market, dessert.
*Fruit brix*.—14-18%.
*Yield*.—Approximately 2.5 bushel/tree at 300 trees/acre annually.

Shipping quality: Good.

Keeping quality: 10 weeks in refrigerated storage.

Tree winter hardiness: Average for domestic apple; depending on acclimation tree is hardy to −10 to −25° F.

Drought resistance: Average for domestic apple.

Disease:
*Resistance*.—Resistant to apple scab (*Venturia inaequalis*); Resistant to fireblight (*Erwinia amylovora*).
*Susceptibility*.—Susceptible to powdery mildew (*Podoshaera leucotricha*) and other fungal diseases; fruit susceptible to soft rot (*Penicillium expansum*).

What is claimed is:

1. A new, distinct variety of apple tree named 'MAIA8', as illustrated and described herein.

* * * * *